(12) United States Patent
Peters et al.

(10) Patent No.: US 10,043,271 B2
(45) Date of Patent: Aug. 7, 2018

(54) DETERMINING AN EFFECTIVE CROSS-SECTIONAL AREA OF A CARDIOVASCULAR STRUCTURE

(71) Applicant: KONINKLIJKE PHILIPS N.V., Eindhoven (NL)

(72) Inventors: Jochen Peters, Hamburg (DE); Juergen Weese, Norderstedt (DE); Irina Waechter-Stehle, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 50 days.

(21) Appl. No.: 15/314,977

(22) PCT Filed: May 21, 2015

(86) PCT No.: PCT/EP2015/061215
§ 371 (c)(1),
(2) Date: Nov. 30, 2016

(87) PCT Pub. No.: WO2015/193055
PCT Pub. Date: Dec. 23, 2015

(65) Prior Publication Data
US 2017/0098302 A1 Apr. 6, 2017

(30) Foreign Application Priority Data
Jun. 19, 2014 (EP) .................................... 14173095

(51) Int. Cl.
*G06K 9/00* (2006.01)
*G06T 7/00* (2017.01)
*A61B 5/02* (2006.01)
*A61B 5/00* (2006.01)
*A61B 5/055* (2006.01)
(Continued)

(52) U.S. Cl.
CPC .......... *G06T 7/0012* (2013.01); *A61B 5/0044* (2013.01); *A61B 5/02028* (2013.01); *A61B 5/055* (2013.01); *A61B 6/032* (2013.01); *A61B 6/503* (2013.01); *G06T 7/11* (2017.01); *G06T 2207/10028* (2013.01); *G06T 2207/10081* (2013.01); *G06T 2207/10088* (2013.01);
(Continued)

(58) Field of Classification Search
USPC ........................................................ 382/131
See application file for complete search history.

(56) References Cited

U.S. PATENT DOCUMENTS

2007/0167913 A1* 7/2007 Elkins ...................... A61F 2/07
604/158
2009/0123050 A1 5/2009 Ionasec et al.
(Continued)

OTHER PUBLICATIONS

Feuchtner, G.M. et al., "Multislice Computed Tomography for Detection of Patients with Aortic Valve Stenosis and Quantification of Severity", Journal of the American College of Cardiology, 2006, 47(7), ABSTRACT.
(Continued)

*Primary Examiner* — Jerome Grant, II

(57) ABSTRACT

The cross-sectional area of a tubular cardiovascular structure to assess blood flow wherein the segmentation of the lumen is applied with a deformable model to the three-dimensional image and fitting the deformable model to the three-dimensional image to obtain a fitted model representing the segmentation of the lumen.

13 Claims, 5 Drawing Sheets

(51) Int. Cl.
*A61B 6/03* (2006.01)
*A61B 6/00* (2006.01)
*G06T 7/11* (2017.01)

(52) U.S. Cl.
CPC ............... *G06T 2207/10136* (2013.01); *G06T 2207/30048* (2013.01); *G06T 2207/30104* (2013.01)

(56) References Cited

U.S. PATENT DOCUMENTS

| | | | |
|---|---|---|---|
| 2010/0232645 A1 | 9/2010 | Blaffert et al. | |
| 2012/0022843 A1 | 1/2012 | Ionasec et al. | |
| 2012/0134564 A1 | 5/2012 | Zheng et al. | |
| 2013/0039554 A1 | 2/2013 | Awechter-Stehle et al. | |
| 2013/0066229 A1 | 3/2013 | Wolff | |
| 2013/0155064 A1 | 6/2013 | Grbic et al. | |
| 2014/0071125 A1 | 3/2014 | Burlina et al. | |
| 2014/0200461 A1* | 7/2014 | Zhang | A61B 6/481 600/481 |
| 2014/0249386 A1* | 9/2014 | Caron | G01F 1/6884 600/301 |
| 2016/0367154 A1* | 12/2016 | Gladshtein | A61B 5/0261 |
| 2017/0119463 A1* | 5/2017 | Srivastava | A61B 18/1492 |
| 2017/0181701 A1* | 6/2017 | Fehrenbacher | A61B 5/4887 |

OTHER PUBLICATIONS

Westermann, Y. et al., "Planimetry of the aortic valve orifice area: Comparison of mutli-slice spiral CT and MRI", European Journal of Radiology, 2011, 77, ABSTRACT.
Lesage, D. et al., "A review of 3D vessel lumen segmentation techniques: Models, features and extraction schemes", Medical Image Analysis 13 (2009), ABSTRACT.
Labounty, T.M. et al., "Aortic valve area on 64-MDCT correlates with transesophageal echocardiography in aortic stenosis", AJR Am J Roentgenol. Dec. 2008;191(6):1652-8. doi: 10.2214/AJR.07.3703.
Cuellar, H. et al., "Cardiac computed tomography for valve disease", La tomografía computarizada cardiaca en la afección valvular. Radiología. 2012. http://dx.doi.org/10.1016/j.rx.2012.05.006.
Feuchtner, G.M. et al., "Sixty-four slice CT evaluation of aortic stenosis using planimetry of the aortic valve area", AJR Am J Roentgenol. Jul. 2007;189(1):197-203.
Ecabert, O. et al., "Segmentation of the heart and great vessels in CT images using a model-based adaptation framework" . Medical Image Analysis 2011, 15(6), ABSTRACT.
Lehmann, H. et al., "Integrating viability information into a cardiac model for interventional guidance", Proc. of FIMH 2009, Lecture Notes in Computer Science 5528, ABSTRACT.
http://en.wikipedia.org/wiki/Pulsatile_flow.
http://www.cims.nyu.edu/~griffith/movies/101220/valve_flow_side.

* cited by examiner

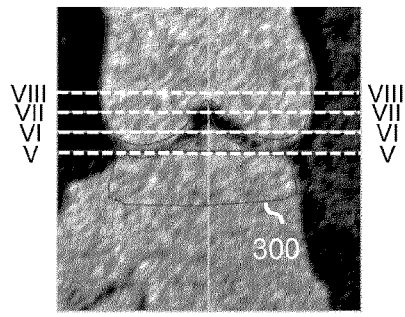
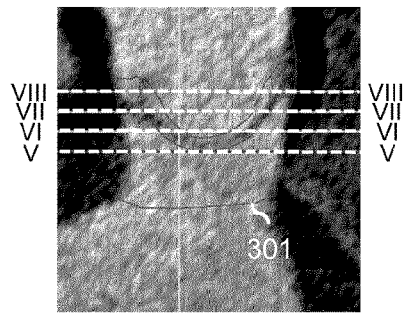
Fig. 4a  Fig. 4b
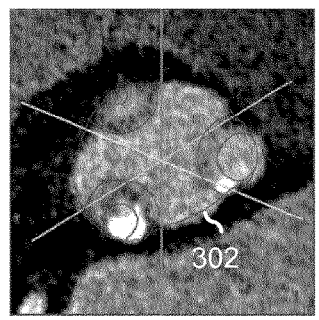
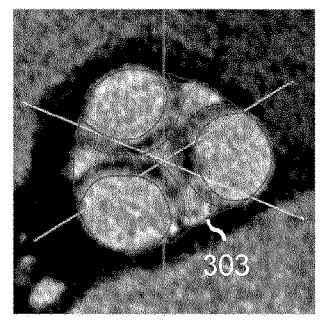
Fig. 5  Fig. 6
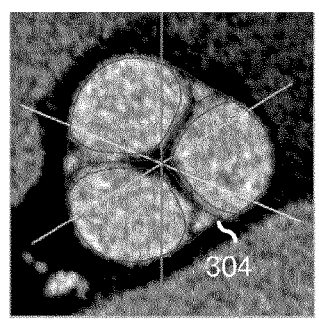
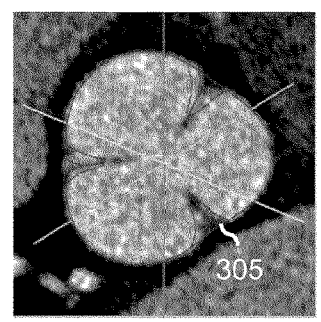
Fig. 7  Fig. 8

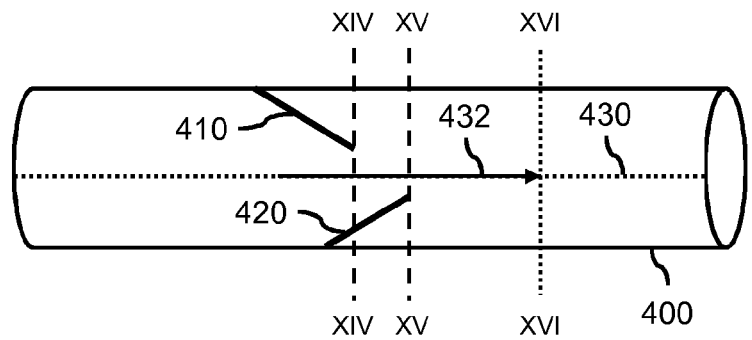
Fig. 13
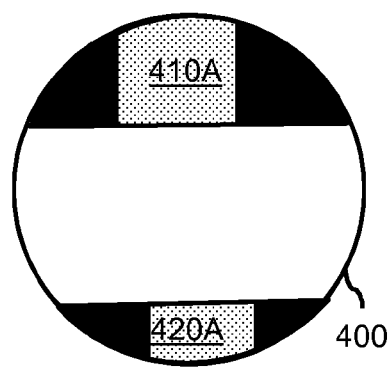 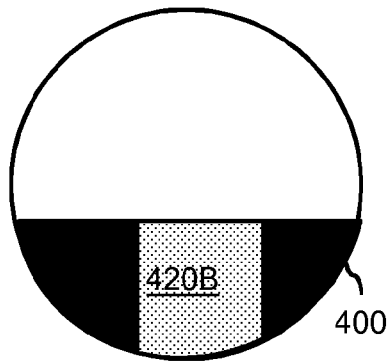
Fig. 14    Fig. 15
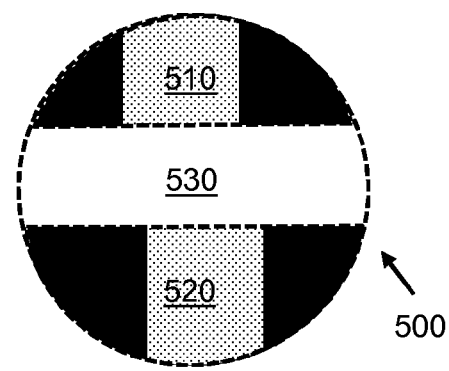
Fig. 16

DETERMINING AN EFFECTIVE CROSS-SECTIONAL AREA OF A CARDIOVASCULAR STRUCTURE

CROSS-REFERENCE TO PRIOR APPLICATIONS

This application is the U.S. National Phase application under 35 U.S.C. § 371 of International Application No. PCT/EP2015/061215, filed on May 21, 2015, which claims the benefit of European Patent Application No. 14173095.2, filed on Jun. 19, 2014. These applications are hereby incorporated by reference herein.

FIELD OF THE INVENTION

The invention relates to a system and a method for determining an effective cross-sectional area of a tubular cardiovascular structure. The invention further relates to a workstation and imaging apparatus comprising the system and to a computer program product comprising instructions for causing a processor system to perform the method.

BACKGROUND OF THE INVENTION

In the medical field, the assessment of blood flow through a tubular cardiovascular structure frequently plays an important role, for example, in order to assess the severity of stenosis of the tubular cardiovascular structure. An example of such a tubular cardiovascular structure is the aortic valve (AV). Degenerative aortic valve stenosis (AS) is the second most common cardiovascular disease, having an incidence rate of 2-7% in the Western European and North American populations aged beyond 65 years. Management of patients with degenerative AS typically depends on the severity of the disease.

For ca. 60-70% of patients, Ultrasound (US) may be used to image the aortic valve and to measure blood velocities via Doppler measurements. In case of a severe enough stenosis of the aortic valve, the effective opening area of the aortic valve is reduced, resulting in the blood flowing at higher velocities. Such higher blood flow velocities show up in the Doppler measurements and are associated with an increased pressure drop across the aortic valve and, accordingly, considered as indicator of aortic valve stenosis.

Alternatively, the degree of stenosis may be assessed from image data obtained by, example, Computed Tomography (CT) or Magnetic Resonance Imaging (MRI) As a result, a three-dimensional image of the cardiovascular structure may be acquired. In case of an aortic valve, Electrocardiography (ECG) gating may be employed to reconstruct or acquire the image(s) from a selected narrow cardiac phase interval, thereby obtaining a three-dimensional image that shows the aortic valve in its relatively short open state. Having obtained image data showing the valve opening, the valve opening may be measured by obtaining angulated cut planes through the three-dimensional image and delineating the apparent valve opening in said cut planes. This technique is referred to AV area planimetry, as described by, e.g., G. M. Feuchtner et al. in "*Multislice Computed Tomography for Detection of Patients With Aortic Valve Stenosis and Quantification of Severity*", Journal of the American College of Cardiology 2006, 47 (7), 1410-1417, as well as by Y. Westermann et al. in "*Planimetry of the aortic valve orifice area: Comparison of multi-slice spiral CT and MRI*", European Journal of Radiology 2011, 77, 426-435.

The measured area of the apparent valve opening may be used to assess the degree of stenosis, namely by applying the measured area in Bernoulli's equation to compute the pressure drop across a narrowing of the tubular cardiovascular structure in a steady-state flow scenario. Here, an area may be deemed the 'effective' cross-sectional area of the tubular cardiovascular structure if its use within Bernoulli's equation yields a similar pressure drop as that obtained by so-termed Computational Fluid Dynamics (CFD)-based blood flow simulations. Besides assessing the degree of stenosis in the aortic valve, the effective cross-sectional area of a tubular cardiovascular structure also plays a role in other medical applications, such as in aortic coarctation where the (thoracic) aorta shows a narrowing.

A problem of the use of area planimetry is that it is insufficiently accurate in estimating the effective cross-sectional area of a tubular cardiovascular structure.

SUMMARY OF THE INVENTION

It would be advantageous to have a system or method for providing a more accurate estimate of the effective cross-sectional area of a tubular cardiovascular structure.

To better address this concern, a first aspect of the invention provides a system for determining an effective cross-sectional area of a tubular cardiovascular structure to enable assessment of blood flow through the tubular cardiovascular structure, the system comprising:

an image interface for obtaining a three-dimensional image of the tubular cardiovascular structure;

a segmentation subsystem for segmenting the three-dimensional image to obtain a segmentation of a lumen inside the tubular cardiovascular structure;

an analysis subsystem configured for:
i) determining a centerline of the tubular cardiovascular structure, the centerline representing an assumed direction of blood flow through the lumen;
ii) using the segmentation of the lumen, determining an apparent flow aperture of the tubular cardiovascular structure in a direction of the centerline; and
iii) determining the effective cross-sectional area of the tubular cardiovascular structure based on the apparent flow aperture;

wherein the segmentation subsystem is configured for obtaining the segmentation of the lumen of the tubular cardiovascular structure by applying a deformable model to the three-dimensional image, the deformable model comprising a representation of the lumen of the type of tubular cardiovascular structure, said applying comprising fitting the deformable model to image data of the three-dimensional image to obtain a fitted model representing the segmentation of the lumen;

wherein the deformable model represents a plurality of anatomical landmarks, and wherein the analysis subsystem is configured for determining the centerline of the tubular cardiovascular structure based on positions of the plurality of the anatomical landmarks in the fitted model.

A further aspect of the invention provides a method for determining an effective cross-sectional area of a tubular cardiovascular structure to enable assessment of blood flow through the tubular cardiovascular structure, the method comprising:

obtaining a three-dimensional image of the tubular cardiovascular structure;

segmenting the three-dimensional image to obtain a segmentation of a lumen inside the tubular cardiovascular structure;

determining a centerline of the tubular cardiovascular structure, the centerline representing an assumed direction of blood flow through the lumen;

using the segmentation of the lumen, determining an apparent flow aperture of the tubular cardiovascular structure in a direction of the centerline; and determining the effective cross-sectional area of the tubular cardiovascular structure based on the apparent flow aperture;

wherein the segmentation subsystem is configured for obtaining the segmentation of the lumen of the tubular cardiovascular structure by applying a deformable model to the three-dimensional image, the deformable model comprising a representation of the lumen of the type of tubular cardiovascular structure, said applying comprising fitting the deformable model to image data of the three-dimensional image to obtain a fitted model representing the segmentation of the lumen;

wherein the deformable model represents a plurality of anatomical landmarks, and wherein the analysis subsystem is configured for determining the centerline of the tubular cardiovascular structure based on positions of the plurality of the anatomical landmarks in the fitted model.

A further aspect of the invention provides a computer program product comprising instructions for causing a processor system to perform the method.

The above measures involve obtaining a three-dimensional image which shows at least a tubular cardiovascular structure. Here, the term 'tubular cardiovascular structure' refers to a cardiovascular structure which allows for the passage of blood through its hollow, tube-shaped interior, i.e., its lumen. Examples of such cardiovascular structures include vessels, valve segments, etc. The three-dimensional image may be, e.g., a volumetric image, or may be constituted by a stack of slices, and may be acquired by various imaging modalities such as Computed Tomography (CT) and Magnetic Resonance Imaging (MRI).

Having obtained the three-dimensional image, the three-dimensional image is segmented, resulting in a three-dimensional segmentation of the lumen. Segmentation of anatomical structures in medical images is well known. For example, a deformable model may be applied to the image data. Another example is that region growing may be used, making use of the fact that blood-pools appear brighter than their surroundings in CT angiography. As a result, a three-dimensional segmentation of the lumen is obtained, typically in the form of data representing the three-dimensional outline of the lumen.

The above measures further involve analyzing the three-dimensional image to determine an effective cross-sectional area of the tubular cardiovascular structure. Here, the adjective 'effective' indicates that the result does not necessarily constitute an actual, clearly identifiable area, but rather that it aims to, when used in Bernoulli's equation, produce a similar pressure drop as would be obtained by CFD-based blood flow simulations.

Determining the effective cross-sectional area involves determining a measure termed 'apparent' flow aperture, which involves determining a centerline of the tubular cardiovascular structure which is assumed to indicate the main streamline(s) of blood flow through the cardiovascular structure, and determining, using the segmentation of the lumen, the flow aperture of the tubular cardiovascular structure in a direction of the centerline. Effectively, the thus-determined apparent flow aperture corresponds to the cross-sectional area of the cardiovascular structure available for unhindered passage of straight streamlines of blood, i.e., passing in parallel along the centerline of the cardiovascular structure.

The present invention is based on the insight that tubular cardiovascular structures frequently have complex interiors which can only be insufficiently assessed using 2D measurements such as area planimetry. For example, in case of an aortic valve, area planimetry involves carrying out 2D measurements on 2D cuts through the aortic valve. However, such 2D measurements do not sufficiently take into account whether the leaflets of the aortic valve meet at commissure lines further downstream. Accordingly, area planimetry systematically overestimates the effective cross-sectional area of the aortic valve.

By obtaining a 3D segmentation of the lumen of the cardiovascular structure and subsequently determining the apparent flow aperture from this segmentation, a measure is obtained which inherently takes into account the 3D shape of the lumen of the cardiovascular structure. By determining the effective cross-sectional area based on this apparent flow aperture, a more accurate estimate is obtained than by area planimetry alone.

It has been found that the effective cross-sectional area, as determined in the claimed manner, correlates very well with CFD-based blood flow simulations. CFD-based blood flow simulations are known to provide accurate estimates of the pressure drop across cardiovascular structures, but are time-consuming and require a high degree of expertise to successfully carry out. However, in an experimental validation for 22 patients with varying degrees of aortic valve stenosis, i.e., from healthy to stenosed, the pressure drop according to CFD-based blood flow simulations was compared to the pressure drop determined by applying the apparent flow aperture in Bernoulli's equation. Both pressure drops show excellent correlation with $R^2 > 0.98$ across a large range of values.

It is known per se to segment anatomical structures in medical images using deformable models. Such type of segmentation is an example of model-based segmentation. For example, the deformable model may be a mean shape model representing a mean shape of the cardiovascular structure across a plurality of patients, or a patient adapted model adapted for the cardiovascular structure of a patient. As such, the deformable model may define a geometry of the type of cardiovascular structure, e.g., as a multi-compartmental mesh of triangles, in particular one which models the hollow, tube-shaped interior of such cardiovascular structures. The deformable model may be represented by model data. The claimed segmentation using a deformable model is well suited for obtaining an accurate 3D segmentation of the lumen of the cardiovascular structure.

The centerline of a tubular cardiovascular structure typically has a known relation to certain anatomical landmarks. By providing a deformable model which encodes such anatomical landmarks, the centerline of the cardiovascular structure may be determined based on the positions of the anatomical landmarks in the deformable model after having been fitted to the image data of the cardiovascular structure.

Optionally, the analysis subsystem is configured for determining the apparent flow aperture by:

i) projecting the segmentation of the lumen along the direction of the centerline to obtain a projection of interior parts of the tubular cardiovascular structure forming obstacles for the blood flow parallel to the centerline; and ii) determining the apparent flow aperture by determining an area in the projection which is free of said projected interior parts.

Projection is well suited for determining the apparent flow aperture of the tubular cardiovascular structure. Namely, from the projection, e.g., onto a projection plane, the apparent flow aperture may be determined as the area in the projection which is free of projected interior parts of the cardiovascular structure and thus represents an aperture which is not blocked by obstacles reaching into the lumen upstream or downstream in the direction of the center line. For example, in case of a parallel projection, this area represents the aperture available for unhindered, straight-line flow through the cardiovascular structure.

Optionally, the positions of the plurality of the anatomical landmarks define a cross-sectional plane through the tubular cardiovascular structure, and the analysis subsystem is configured for determining the centerline by determining a line orthogonal to the cross-sectional plane. For example, in case of an aortic valve, the anatomical landmarks may define the three hinge points, i.e., the lowest points, of each leaflet at the bulbus wall. The cross-sectional plane defined by these three points is known to be oriented approximately perpendicular to the aortic centerline. Accordingly, the system is enabled to determine the aortic centerline, namely as the line orthogonal to the cross-sectional plane.

Optionally, the analysis subsystem is configured for determining the centerline of the tubular cardiovascular structure by:

i) for each of a plurality of candidate center lines, determining the apparent flow aperture of the tubular cardiovascular structure; and ii) selecting one of the plurality of candidate center lines which maximizes the apparent flow aperture.

Optionally, the analysis subsystem is configured for determining the effective cross-sectional area of the tubular cardiovascular structure as a weighted average of i) the apparent flow aperture of the tubular cardiovascular structure, and ii) a cross-sectional area of the tubular cardiovascular structure as determined by area planimetry. While the cross-sectional area determined by area planimetry likely overestimates the effective cross-sectional area of the aortic valve, the apparent flow aperture may, whilst being overall more accurate, underestimate this cross-sectional area. A weighted average of the apparent flow aperture and the cross-sectional area as determined by area planimetry may provide an even more accurate estimate. For example, both measures may be averaged. Advantageously, the effective cross-sectional area, as determined in the claimed manner, provides nearly the same results as CFD-based blood flow simulations.

Optionally, the analysis subsystem is configured for performing the area planimetry using the segmentation of the lumen.

Optionally, the analysis subsystem is configured for determining a pressure drop across the tubular cardiovascular structure by applying the effective cross-sectional area in Bernoulli's equation.

Optionally, the analysis subsystem is configured for applying the effective cross-sectional area in Bernoulli's equation to assess a degree of stenosis in the tubular cardiovascular structure.

Optionally, the tubular cardiovascular structure comprises an aortic valve, and the centerline is an aortic centerline. The claimed measures are well suited for, but not limited to, determining the cross-sectional area of the aortic valve.

A further aspect of the invention provides a workstation or imaging apparatus comprising the system. Accordingly, the workstation or imaging apparatus may each comprise the image interface, the segmentation subsystem and the analysis subsystem.

It will be appreciated by those skilled in the art that two or more of the above-mentioned embodiments, implementations, and/or aspects of the invention may be combined in any way deemed useful.

Modifications and variations of the imaging apparatus, the workstation, the method, and/or the computer program product, which correspond to the described modifications and variations of the system, can be carried out by a person skilled in the art on the basis of the present description.

A person skilled in the art will appreciate that the method may be applied to multi-dimensional image data, e.g., to three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

FIGS. 4a and 4b show cut planes through a 3D image of an aortic valve in its closed state, the cut planes being parallel to the aortic centerline;

FIGS. 5-8 show cut planes perpendicular to the aortic centerline at different positions along the aortic valve, as indicated in FIGS. 4a-4b;

FIG. 13 schematically shows a tubular cardiovascular structure;

FIGS. 14 and 15 show cross-sectional views of the tubular cardiovascular perpendicular to, and at different positions along, the aortic centerline;

FIG. 16 shows a projection of a segmentation of the lumen of the tubular cardiovascular structure along the direction of the centerline;

DETAILED DESCRIPTION OF EMBODIMENTS

Figure 1:
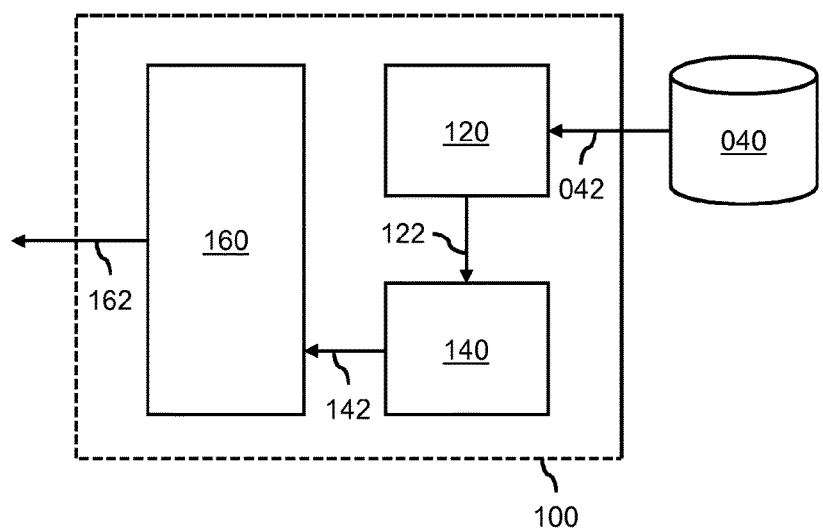
FIG. 1 shows a system for determining an effective cross-sectional area of a tubular cardiovascular structure from a 3D image of the tubular cardiovascular structure.

FIG. 1 shows a system 100 for determining an effective cross-sectional area of a tubular cardiovascular structure to enable assessment of blood flow through the tubular cardiovascular structure. The system 100 comprises an image interface 120 for obtaining a three-dimensional [3D] image 122 of the tubular cardiovascular structure. FIG. 1 shows the image interface 120 obtaining the 3D image 122 in the form of image data 042 from an external database 040, such as a Picture Archiving and Communication System (PACS). As such, the image interface 120 may be constituted by a so-termed DICOM interface. However, the image interface 120 may also take any other suitable form, such as an internal or external memory or storage interface, a network interface to local or wide area network, etc.

The system 100 further comprises a segmentation subsystem 140. The segmentation subsystem 140 is configured for, during operation of the system 100, segmenting the three-dimensional image to obtain a segmentation of a lumen inside the tubular cardiovascular structure. For that purpose, the segmentation subsystem 140 is shown to obtain the 3D image 122 via the image interface 120, and to output segmentation data 142 representing the segmentation of the lumen of the tubular cardiovascular structure.

The system 100 further comprises an analysis subsystem 160. The analysis subsystem 160 is configured for, during operation of the system 100,
i) determining a centerline of the tubular cardiovascular structure, the centerline representing an assumed direction of blood flow through the lumen;
ii) using the segmentation of the lumen, determining an apparent flow aperture of the tubular cardiovascular structure in a direction of the centerline; and
iii) determining the effective cross-sectional area of the tubular cardiovascular structure based on the apparent flow aperture.

FIG. 1 shows the analysis subsystem 160 outputting data 162 representing a result of its analysis, such as a data-representation of the effective cross-sectional area. Accordingly, the result of the analysis may be used in further analysis, visualization, etc.

It is noted that the operation of the system 100, including various optional aspects thereof, will be further described with reference to FIGS. 13 to 17b.

The system 100 may be embodied as, or in, a single device or apparatus, such as a workstation or imaging apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system may be implemented in the device or apparatus in the form of programmable logic, e.g., as a Field-Programmable Gate Array (FPGA). It is noted that the system 100 may also be implemented in a distributed manner, i.e., involving different devices or apparatuses.

Figure 2:
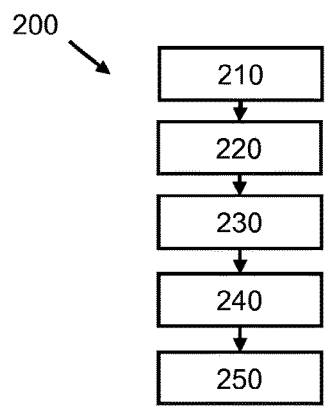
FIG. 2 shows a method for determining the effective cross-sectional area of the tubular cardiovascular structure from the 3D image of the tubular cardiovascular structure.

FIG. 2 shows a method 200 for determining an effective cross-sectional area of a tubular cardiovascular structure to enable assessment of blood flow through the tubular cardiovascular structure. The method 200 comprises, in an operation titled "OBTAINING IMAGE OF TUBULAR CARDIOVASCULAR STRUCTURE", obtaining 210 a three-dimensional image of the tubular cardiovascular structure. The method 200 further comprises, in an operation titled "SEGMENTING LUMEN OF TUBULAR CARDIOVASCULAR STRUCTURE", segmenting 220 the three-dimensional image to obtain a segmentation of an lumen of the tubular cardiovascular structure. The method 200 further comprises, in an operation titled "DETERMINING CENTERLINE OF TUBULAR CARDIOVASCULAR STRUCTURE", determining 230 a centerline of the tubular cardiovascular structure, the centerline representing an assumed direction of blood flow through the lumen. The method 200 further comprises, in an operation titled "DETERMINING APPARENT FLOW APERTURE", using the segmentation of the lumen, determining 240 an apparent flow aperture of the tubular cardiovascular structure in a direction of the centerline. The method 200 further comprises, in an operation titled "DETERMINING EFFECTIVE CROSS-SECTIONAL AREA BASED ON DETERMINED APPARENT FLOW APERTURE", determining 250 the effective cross-sectional area of the tubular cardiovascular structure based on the apparent flow aperture.

Figure 3:
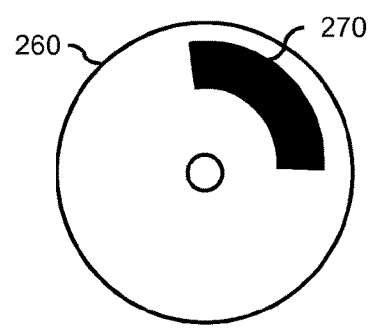
FIG. 3 shows a computer program product comprising instructions for causing a processor system to perform the method.

The method 200 may be implemented on a computer as a computer implemented method, as dedicated hardware, or as a combination of both. As illustrated in FIG. 3, instructions for the computer, i.e., executable code, may be stored on a computer program product 260, e.g., in the form of a series 270 of machine readable physical marks and/or as a series of elements having different electrical, e.g., magnetic, or optical properties or values. The executable code may be stored in a transitory or non-transitory manner. Examples of computer program products include memory devices, optical storage devices 260, integrated circuits, servers, online software, etc. FIG. 3 shows an optical disc.

The operation of the system of FIG. 1 and the method of FIG. 2, including various optional aspects thereof, may be explained in more detail as follows. Here, the aortic valve is selected as a non-limiting example of a tubular cardiovascular structure.

FIGS. 4a-12 illustrate a problem of area planimetry, in that only two-dimensional [2D] cut plane(s) are analyzed. In case of a tubular cardiovascular structure such as the aortic valve, this may lead to an overestimation of the effective cross-sectional area of the aortic valve. Namely, in the case of an aortic valve, area planimetry does not take into account whether the aortic leaflets meet downstream at commissure lines. The impact on the 3D blood flow can thus not be fully assessed by such 2D measurements. As a result, the relation between the measured areas and the physiological impact, such as increased pressure gradients, is unclear. It is noted that other tubular cardiovascular structures may have similar changes in internal structures along their longitudinal direction. Therefore, also here area planimetry may lead to an overestimation of the effective cross-sectional area.

FIGS. 4a and 4b show cut planes through a 3D image of the aortic valve in its closed state. Here, the cut planes are perpendicular to the aortic centerline, and in particular through the surface of the aortic leaflets towards the left ventricle [LV] and the Left Ventricular Outflow Tract [LVOT]-wall. In both Figs., the contour lines 300, 301 represent a tubular model which covers part of the LVOT. Here, the parallel pairs of curved lines, being part of the contour lines 300, 301, delineate the boundary of the leaflets.

Figure 9:
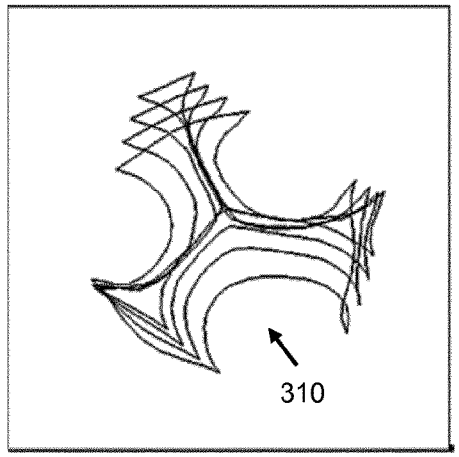
FIGS. 9 and 10 shows contour stacks obtained from the perpendicular cut planes of the aortic valve in its closed state, with FIG. 9 being obtained from cut planes nearby the hinge points upstream in the aortic flow and FIG. 10 being obtained from cut planes nearby the commissure points downstream in the aortic flow.
Figure 10:
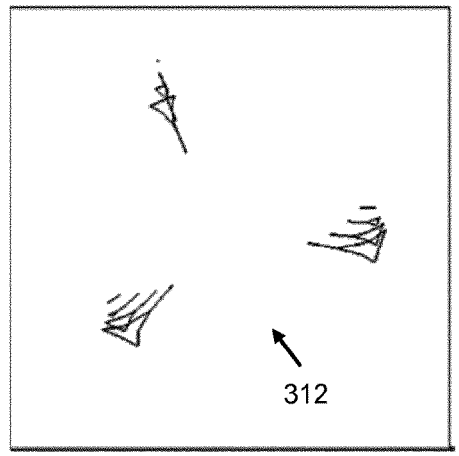

FIGS. 5-8 show cut planes perpendicular to the aortic centerline at different positions along said centerline, namely along the lines V-V, VI-VI, VII-VII and VIII-VIII, respectively, indicated in FIGS. 4a-4b. In FIGS. 5-8, the contour lines 302-305 represent the aortic bulbus and their parallel pairs of curved lines delineate the boundary of the leaflets FIGS. 9 and 10 show contour stacks obtained at different longitudinal positions along the aortic centerline, i.e., at different heights of the aortic valve. Depending on the position of the 2D cut plane along the aortic centerline, initially closed elliptic contours are obtained if the LVOT wall is cut below the aortic valve. Then, further downstream, deformed triangular contours are obtained (FIG. 9). Finally, when proceeding downstream until the commissure points where the aortic leaflets meet each other at the aortic bulbus wall, the contours break apart (FIG. 10). As can be recognized in FIGS. 9 and 10, area planimetry may lead to an overestimation of the effective cross-sectional area of the aortic value, since the effective cross-sectional area estimated from the cut-planes far below the commissure points (FIG. 9), i.e., at longitudinal positions where the contours are still closed, may be subsequently blocked by the aortic leaflets at the commissure points (FIG. 10).

Figure 11:
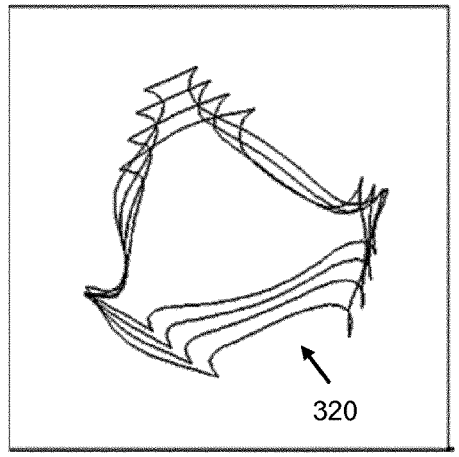
FIGS. 11 and 12 differ from FIGS. 9 and 10, respectively, in that the depicted contour stacks are obtained from the aortic valve in its open state.
Figure 12:
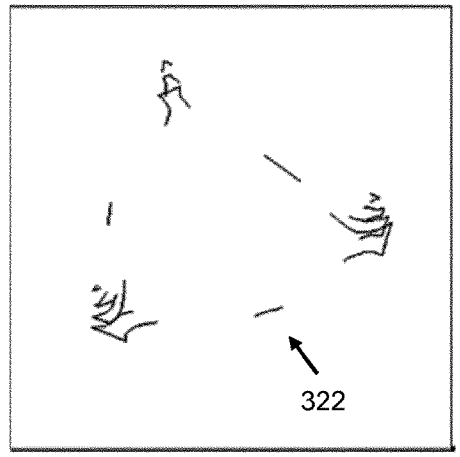

FIGS. 11 and 12 correspond to FIGS. 9 and 10, respectively, but show the aortic valve in its open state rather than in its closed state. Here, FIG. 11 shows deformed triangular contours 320 whilst the contours 322 in FIG. 12 are shown to break apart.

The system and method as claimed are based at least in part on the consideration of streamlines of blood passing through the tubular cardiovascular structure. FIG. 13 schematically shows a tubular cardiovascular structure 400, along with its centerline 430. The tubular cardiovascular structure 400 is shown to comprise anatomical parts 410, 420 which protrude into its lumen. For example, in the case of the aortic valve, such anatomical parts may be aortic leaflets. It is noted, however, that the lumen of a tubular cardiovascular structure may have a complex interior shape for other reasons as well.

As a result of the anatomical parts 410, 420 protruding into the lumen of the tubular cardiovascular structure, the cross-sections of said structure along the lines XIV-XIV and XV-XV, as shown in FIGS. 14 and 15, respectively, show different parts 410A, 420A, 420B of the anatomical parts 410, 420 blocking the blood flow in the lumen of the tubular cardiovascular structure. In particular, FIGS. 14 and 15 show a difference in non-obstructed, i.e., free or non-blocked area, being only in part overlapping along the centerline.

The effective cross-sectional area may be determined by determining an apparent flow aperture of the tubular cardiovascular structure 400 in the direction of the centerline 430. The apparent flow aperture may be determined in various ways.

In one embodiment, the apparent flow aperture may be determined by projecting the segmentation of the lumen along the direction of the centerline, i.e., in a projection direction 432, to obtain a projection of the segmentation. In the example of FIG. 13, the projection plane is indicated in the form of the line XVI-XVI, with FIG. 16 showing the obtained projection 500. It can be seen that the anatomical parts 410, 420 are represented by projected parts 510, 520 in the projection 500. The apparent flow aperture may be determined as the area 530 which is free of said projected parts 510, 520. As such, the free area 530 represents the aperture available for streamlines of blood flowing straight along the aortic centerline, and therefore may be termed as 'apparent' flow aperture.

It is noted that, instead of explicitly projecting the segmentation of the lumen along the direction of the centerline, the segmentation may also be analyzed in different, yet functionally equivalent manners, e.g., by propagating stream lines through the segmentation of the lumen and determining the apparent flow aperture from those stream lines which are not blocked by the lumen. Another example is that 2D cut planes may be each segmented to provide a binary mask representing the interior area. For that purpose, a region growing-based segmentation technique may be used which makes use of the fact that blood pools appear brighter than their surroundings in CT angiography. The binary masks, when combined or stacked, provide a 3D segmentation of the lumen of the tubular cardiovascular structure. The binary masks may then be combined by a logical conjunction ('AND') to determine a binary mask representing the apparent flow aperture. It will be appreciated that various other embodiments are within reach of the skilled person as well.

For obtaining the segmentation of the lumen of the tubular cardiovascular structure, a deformable model may be used. The deformable model may comprise a representation of the lumen of the type of tubular cardiovascular structure, e.g., in the form of a mesh. It is noted that it is known per se to use deformable models to segment tubular cardiovascular structures, as described in, e.g., "*A review of 3D vessel lumen segmentation techniques: Models, features and extraction schemes*" by Lesage et al., Medical Image Analysis 13 (2009), pp. 819-845. The segmentation subsystem may be configured for fitting such a deformable model to the image data of the three-dimensional image to obtain a fitted model representing the segmentation of the lumen. Accordingly, the fitted model may be projected along the centerline, or analyzed in a functionally equivalent manner, to determine the apparent flow aperture. It is noted that, instead of deformable models, also other types of model-based segmentation may be used to obtain a mesh-based segmentation of the lumen.

Having obtained such a mesh-based segmentation of the lumen, the projection may be performed in the following manner. Here, it is assumed that the tubular cardiovascular structure is an aortic valve. To implement a measurement of the apparent flow aperture, the mesh may be provided with auxiliary triangles that connect the free edges of the leaflets. These triangles cover the complete so-called valve orifice (the free lumen) between the free leaflet edges. Each triangle may have an orientation, as per the model's design, such that its outward normal points from the LV into the aorta. These outward normals may be calculated via the cross product $N=(v_2-v_1)\times(v_3-v_1)$ where $v_{1,2,3}$ are the vertices of the triangle. The length $|N|$ encodes twice the triangle area, and the normalized direction $N/|N|$ encodes the outward normal direction. The projected area of a single triangle onto a projection plane, such as the valve plane, with normal n may be calculated by the scalar product $n \cdot N/2$. Positive values indicate that the triangle normal $N/|N|$ and the plane normal n have a consistent orientation, in that their relative angle is below 90 degrees. Assuming that none of the interior triangles is flipped due to crossing aortic leaflets, the projection of each triangle 'i' onto the valve plane with normal n (also pointing from the LV into the aorta) yields a positive contribution $n \cdot N_i/2$. The overall projected interior area may then obtained as a sum over all interior triangles 'i', i.e., $n \cdot (\Sigma_i N_i)/2$.

An embodiment of the projection may thus calculate the sum over all $N_i$, project them onto the valve plane normal n, and divide the result by 2. To obtain the maximum projected area, $\Sigma i \ Ni$ may, instead of being projected onto the valve plane normal n, be projected onto its own direction, e.g., by dividing the length of $\Sigma_i N_i$ by 2.

Figure 17A:
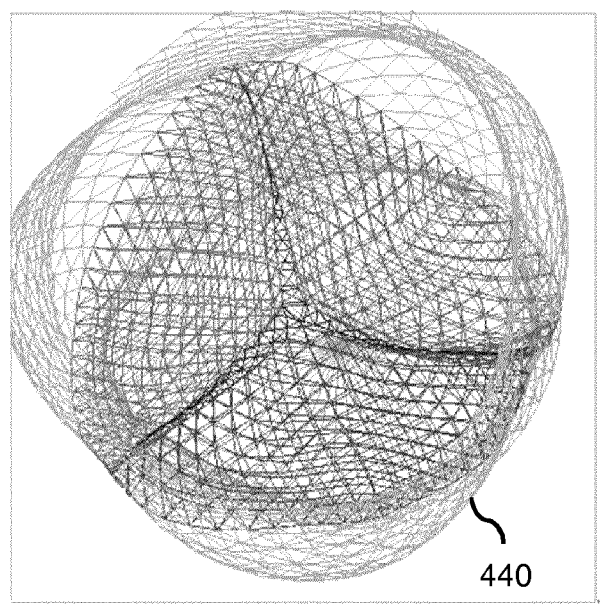
FIG. 17a shows the mesh of a deformable model fitted to an aortic valve.
Figure 17B:
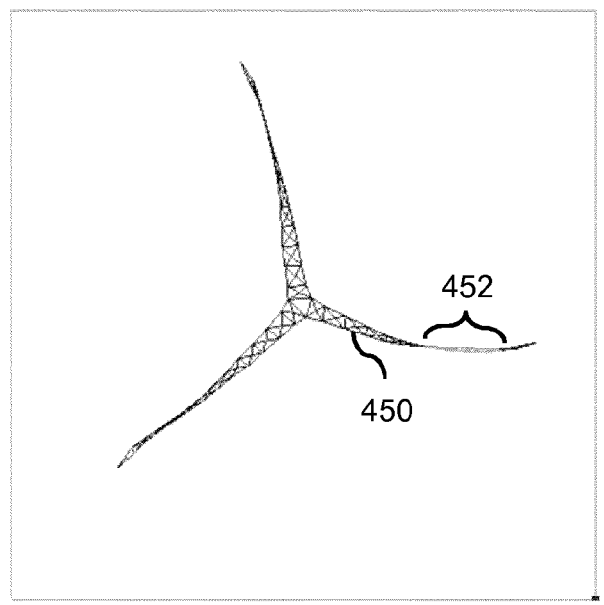
FIG. 17b illustrates a local crossing of aortic leaflets in the mesh.

Another embodiment of the projection may take into account subtle distinction between normally oriented, versus flipped, interior triangles. Due to small errors in the segmentation, the aortic leaflets may cross locally in the segmentation, in particular in the closed state of the aortic valve. FIG. 17a shows the mesh 440 of a deformable model fitted to the aortic valve in its closed state. FIG. 17b shows a part 450 of the mesh, namely that representing the valve orifice. Indicated are triangles 452 representing such local crossing of the aortic leaflets. These local crossings may be detected by calculating the projected areas using the above formula $n \cdot N_i/2$ for each triangle 'i'. Here, negative values may indicate that the triangle normal does not point from the LV into the aorta but has been flipped into the opposite direction. After detection of such local flips, mesh post-processing steps may be used to resolve the local crossings, i.e., to correct the segmentation. Thereafter, all $n \cdot N_i/2$ yield a contribution $\geq 0$ and the valve area measurement may continue as described above.

In case a deformable model is used for segmenting the lumen of the tubular cardiovascular structure, the deformable model may also be used to determine the centerline of the tubular cardiovascular structure. For example, the deformable model may be configured to represent a plurality of anatomical landmarks from which, after being fitted to the image data, the centerline may be derived. As such, the data representing the deformable model may encode such anatomical landmarks. In a specific example, the positions of the plurality of the anatomical landmarks may define a cross-sectional plane through the tubular cardiovascular structure, and the centerline may be determined as a line orthogonal to the cross-sectional plane. For example, in case of an aortic valve, the anatomical landmarks may represent the lowest points, i.e., the hinge points of the anatomical leaflet at the bulbus wall.

The centerline of the tubular cardiovascular structure may also be determined in other ways. For example, for each of a plurality of candidate center lines, the apparent flow aperture of the tubular cardiovascular structure may be determined, and one of the plurality of candidate center lines may be selected which maximizes the apparent flow aperture. Another example is the use of a distance transformation in combination with front propagation, as described in the above introduced review paper of Lesage et al.

In general, the analysis subsystem may be configured for determining the effective cross-sectional area of the tubular cardiovascular structure as a weighted average of i) the apparent flow aperture of the tubular cardiovascular structure, and ii) a cross-sectional area of the tubular cardiovascular structure as determined by area planimetry. For example, both measurements may be substantially equally weighted. The latter cross-sectional area may be determined by manual area planimetry. Alternatively, the analysis subsystem may automatically perform the area planimetry, e.g., using the segmentation of the lumen. For example, referring to FIGS. 9 and 11, the area of the smallest still-closed cross-sectional contour may be selected as the cross-sectional area in accordance with area planimetry.

Having determined the effective cross-sectional area of the tubular cardiovascular structure, the analysis subsystem may determine a pressure drop across the tubular cardiovascular structure, namely by applying the effective cross-sectional area in Bernoulli's equation. The result may be used to assess a degree of stenosis in the tubular cardiovascular structure. The degree of stenosis may be included in a report, visualized, or in general provided as feedback to a clinician.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for determining an effective cross-sectional area of a tubular cardiovascular structure to enable assessment of blood flow through the tubular cardiovascular structure, the system comprising:
   an image interface for obtaining a three-dimensional image of the tubular cardiovascular structure;
   a segmentation subsystem for segmenting the three-dimensional image to obtain a segmentation of a lumen inside the tubular cardiovascular structure;
   an analysis subsystem configured for:
   i) determining a centerline of the tubular cardiovascular structure, the centerline representing an assumed direction of blood flow through the lumen;
   ii) using the segmentation of the lumen, determining an apparent flow aperture of the tubular cardiovascular structure in a direction of the centerline; and
   iii) determining the effective cross-sectional area of the tubular cardiovascular structure based on the apparent flow aperture;
   wherein the segmentation subsystem is configured for obtaining the segmentation of the lumen of the tubular cardiovascular structure by applying a deformable model to the three-dimensional image, the deformable model comprising a representation of the lumen of the type of tubular cardiovascular structure, said applying comprising fitting the deformable model to image data of the three-dimensional image to obtain a fitted model representing the segmentation of the lumen;
   wherein the deformable model represents a plurality of anatomical landmarks, and wherein the analysis subsystem is configured for determining the centerline of the tubular cardiovascular structure based on positions of the plurality of the anatomical landmarks in the fitted model.

2. The system according to claim 1, wherein the analysis subsystem is configured for determining the apparent flow aperture by:
   i) projecting the segmentation of the lumen along the direction of the centerline to obtain a projection of interior parts of the tubular cardiovascular structure forming obstacles for the blood flow parallel to the centerline; and
   ii) determining the apparent flow aperture by determining an area in the projection which is free of said projected interior parts.

3. The system according to claim 1, wherein the positions of the plurality of the anatomical landmarks define a cross-sectional plane through the tubular cardiovascular structure, and wherein the analysis subsystem is configured for determining the centerline by determining a line orthogonal to the cross-sectional plane.

4. The system according to claim 1, wherein the analysis subsystem is configured for determining the centerline of the tubular cardiovascular structure by:
   i) for each of a plurality of candidate center lines, determining the apparent flow aperture of the tubular cardiovascular structure; and
   ii) selecting one of the plurality of candidate center lines which maximizes the apparent flow aperture.

5. The system according to claim 1, wherein the analysis subsystem is configured for determining the effective cross-sectional area of the tubular cardiovascular structure as a weighted average of i) the apparent flow aperture of the tubular cardiovascular structure, and ii) a cross-sectional area of the tubular cardiovascular structure as determined by area planimetry.

6. The system according to claim 5, wherein the analysis subsystem is configured for performing the area planimetry using the segmentation of the lumen.

7. The system according to claim 1, wherein the analysis subsystem is configured for determining a pressure drop across the tubular cardiovascular structure by applying the effective cross-sectional area in Bernoulli's equation.

8. The system according to claim 7, wherein the analysis subsystem is configured for applying the effective cross-sectional area in Bernoulli's equation to assess a degree of stenosis in the tubular cardiovascular structure.

9. The system according to claim 1, wherein the tubular cardiovascular structure comprises an aortic valve, and wherein the centerline is an aortic centerline.

10. A workstation comprising the system according to claim 1.

11. An imaging apparatus comprising the system according to claim 1.

12. A method for determining an effective cross-sectional area of a tubular cardiovascular structure to enable assessment of blood flow through the tubular cardiovascular structure, the method comprising:
   obtaining three-dimensional image of the tubular cardiovascular structure;
   segmenting the three-dimensional image to obtain a segmentation of a lumen inside the tubular cardiovascular structure;
   determining a centerline of the tubular cardiovascular structure, the centerline representing an assumed direction of blood flow through the lumen;
   using the segmentation of the lumen, determining an apparent flow aperture of the tubular cardiovascular structure in a direction of the centerline; and
   determining the effective cross-sectional area of the tubular cardiovascular structure based on the apparent flow aperture;
   wherein the segmentation subsystem is configured for obtaining the segmentation of the lumen of the tubular cardiovascular structure by applying a deformable model to the three-dimensional image, the deformable model comprising a representation of the lumen of the type of tubular cardiovascular structure, said applying comprising fitting the deformable model to image data of the three-dimensional image to obtain a fitted model representing the segmentation of the lumen;
   wherein the deformable model represents a plurality of anatomical landmarks, and wherein the analysis subsystem is configured for determining the centerline of the tubular cardiovascular structure based on positions of the plurality of the anatomical landmarks in the fitted model.

13. A non-transitory computer program product comprising instructions for causing a processor system to perform the method according to claim 12.

* * * * *